(12) United States Patent
Miyata et al.

(10) Patent No.: US 11,779,524 B2
(45) Date of Patent: *Oct. 10, 2023

(54) PHOTOPOLYMERIZATION INITIATOR COMPRISING AN ARYLIODONIUM SALT FOR DENTAL PHOTOCURABLE COMPOSITIONS

(71) Applicant: KABUSHIKI KAISHA SHOFU, Kyoto (JP)

(72) Inventors: Shunsuke Miyata, Kyoto (JP); Daisuke Hara, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 123 days.

This patent is subject to a terminal disclaimer.

(21) Appl. No.: 17/201,193

(22) Filed: Mar. 15, 2021

(65) Prior Publication Data

US 2021/0283022 A1    Sep. 16, 2021

(30) Foreign Application Priority Data

Mar. 16, 2020 (JP) .................. 2020-045035
Dec. 14, 2020 (JP) .................. 2020-206845

(51) Int. Cl.
  *A61K 6/62* (2020.01)
  *A61K 6/887* (2020.01)
  *C08F 2/50* (2006.01)

(52) U.S. Cl.
  CPC ............... *A61K 6/62* (2020.01); *A61K 6/887* (2020.01); *C08F 2/50* (2013.01)

(58) Field of Classification Search
  CPC ....................................................... A61K 6/62
  See application file for complete search history.

(56) References Cited

U.S. PATENT DOCUMENTS

| | | | |
|---|---|---|---|
| 5,846,075 | A | 12/1998 | Suh et al. |
| 7,084,182 | B2 | 8/2006 | Hara et al. |
| 2005/0123762 | A1 | 6/2005 | Ori et al. |
| 2007/0100020 | A1 | 5/2007 | Nakatsuka et al. |
| 2008/0068862 | A1 | 3/2008 | Shimura |
| 2009/0068123 | A1 | 3/2009 | Takei et al. |
| 2010/0267856 | A1 | 10/2010 | Shinoda et al. |
| 2010/0311858 | A1 | 12/2010 | Holmes et al. |
| 2011/0288195 | A1 | 11/2011 | Kajikawa et al. |
| 2017/0355857 | A1 | 12/2017 | Lee et al. |
| 2018/0214351 | A1 | 8/2018 | Fik et al. |
| 2018/0373145 | A1* | 12/2018 | Shiraishi ............... G03F 7/039 |
| 2019/0388355 | A1 | 12/2019 | Christensen et al. |
| 2020/0069534 | A1 | 3/2020 | Furuhashi et al. |
| 2021/0283022 | A1 | 9/2021 | Miyata et al. |
| 2022/0002453 | A1 | 1/2022 | Hayakawa et al. |

FOREIGN PATENT DOCUMENTS

| | | |
|---|---|---|
| CN | 107922365 | 4/2018 |
| EP | 1 101 484 | 5/2001 |
| EP | 2 163 234 | 3/2010 |
| EP | 2 280 032 | 2/2011 |
| EP | 2 394 628 | 12/2011 |
| EP | 3 398 975 | 11/2018 |
| EP | 3 782 598 | 2/2021 |
| JP | 2001-139843 | 5/2001 |
| JP | 2005-213231 | 8/2005 |
| JP | 2005213231 A * | 8/2005 |
| JP | 2006-76973 | 3/2006 |
| JP | 2006-225350 | 8/2006 |
| JP | 2007-39475 | 2/2007 |
| JP | 4093974 | 6/2008 |
| JP | 4596786 | 12/2010 |
| JP | 4783151 | 7/2011 |
| JP | 5114498 | 10/2012 |
| JP | 5268478 | 5/2013 |
| JP | 5379563 | 10/2013 |
| JP | 5461415 | 1/2014 |
| JP | 5615720 | 9/2014 |
| JP | 2017-119803 | 7/2017 |

(Continued)

OTHER PUBLICATIONS

English machine translation of Akitsumi et al. (JP 2005-213231) (Year: 2005).*
Extended European Search Report (EESR) dated Jun. 25, 2021 in corresponding European Patent Application No. 21162475.4.
Extended European Search Report dated Sep. 7, 2021 in corresponding European Patent Application No. 21162481.2.
Extended European Search Report dated Sep. 9, 2021 in corresponding European Patent Application No. 21162479.6.
Extended European Search Report dated Sep. 7, 2021 in corresponding European Patent Application No. 21162490.3.

(Continued)

*Primary Examiner* — Michael F Pepitone
(74) *Attorney, Agent, or Firm* — WENDEROTH, LIND & PONACK, L.L.P.

(57) ABSTRACT

The present invention provides a photopolymerization initiator capable of exhibiting excellent sensitivity to photopolymerization and ensuring a sufficient pot life under ambient light, and a dental photocurable composition comprising the photopolymerization initiator. More specifically, the present invention provides a photopolymerization initiator (c) used in a dental photocurable composition, comprising: (c-1) a photosensitizer, (c-2) a polymerization accelerator, and (c-3) an aryliodonium salt represented by the formula (1):
[Chemical Formula 1]

$$[(R1)_2I]^+[(R2)_bPF_{6-b}]^- \qquad (1)$$

wherein, R1 represents an organic group bonded to I, R2 represents an alkyl group in which a part of hydrogen atoms is substituted with a flourine atom, and b represents the number thereof which is an integer of from 1 to 5, and a dental photocurable composition comprising the photopolymerization initiator.

6 Claims, No Drawings

(56) References Cited

FOREIGN PATENT DOCUMENTS

| | | | | |
|---|---|---|---|---|
| JP | 2017119803 A | * | 7/2017 | ............... C08F 2/50 |
| JP | 2020-500879 | | 1/2020 | |
| WO | 99/62460 | | 12/1999 | |
| WO | 2006/106838 | | 10/2006 | |
| WO | 2008/068862 | | 6/2008 | |
| WO | 2018/164074 | | 9/2018 | |

OTHER PUBLICATIONS

Extended European Search Report dated Sep. 7, 2021 in corresponding European Patent Application No. 21162495.2.
Extended European Search Report dated Aug. 29, 2022 in corresponding European Patent Application No. 22161514.9.
Extended European Search Report dated Aug. 29, 2022 in corresponding European Patent Application No. 22161538.8.
Extended European Search Report dated Aug. 29, 2022 in corresponding European Patent Application No. 22161548.7.
Markus Griesser et al., "Photoinitiators with β-phenylogous Cleavage: an evaluation of reaction mechanisms and performance", Macromolecules, vol. 45, pp. 1737-1745, 2012.
Shiraishi et al., "Comparison between NIR and UV-Sensitized Radical and Cationic Reactivity of Iodonium Salts Comprising Anions with Different Coordination Behavior", Journal of Photopolymer Science and Technology, 2017, vol. 30 No. 6, pp. 633-638.

* cited by examiner

PHOTOPOLYMERIZATION INITIATOR COMPRISING AN ARYLIODONIUM SALT FOR DENTAL PHOTOCURABLE COMPOSITIONS

CROSS-REFERENCE TO RELATED APPLICATIONS

This application claims priority to Japanese Patent Application No. 2020-045035, filed Mar. 16, 2020, and Japanese Patent Application No. 2020-206845, filed Dec. 14, 2020, which are incorporated by reference herein in their entirety.

TECHNICAL FIELD

The present invention relates to a dental photocurable composition, and a photopolymerization initiator used in the dental photocurable composition.

BACKGROUND ART

In the dental field, dental photocurable compositions are used for oral treatment, and are applied for, for example, dental adhesives, dental composite resins, dental abutment construction materials, dental resin cements, dental surface coatings, dental pit fissure sealing materials, dental manicure materials, and the like.

REFERENCE DOCUMENTS

Patent Documents

Patent Document 1: Japanese Patent No. 4093974 B
Patent Document 2: Japanese Patent No. 4596786 B

SUMMARY OF THE INVENTION

Problems to be Solved by the Invention

Sufficient physical properties, however, could not be obtained by a photopolymerization initiator used in the dental photocurable compositions.

Patent Documents 1 and 2 propose photopolymerization initiators containing a photoacid generator (a triazine compound or a specific aryliodonium salt), a sensitizer, and an electron donor compound, as a photopolymerization initiator. Sufficient physical properties, however, could not be obtained.

There is a demand for a photopolymerization initiator which exhibits excellent sensitivity to photopolymerization and can secure a sufficient pot life under ambient light, and also for providing a dental photocurable composition comprising such the photopolymerization initiator.

Means for Solving the Problems

The present invention relates to a photopolymerization initiator (c) used in a dental photocurable composition, comprising:
(c-1) a photosensitizer,
(c-2) a polymerization accelerator, and
(c-3) an aryliodonium salt represented by the formula (1):
[Chemical Formula 1]

(1)

wherein R1 represents an organic bonded to I, R2 represents an alkyl group in which a part of hydrogen atoms is substituted with a flourine atom, and b represents the number thereof which is an integer of from 1 to 5.

Effects of the Invention

The photopolymerization initiator of the present invention can give a dental photocurable composition which exhibits excellent sensitivity to irradiation light and secures a sufficient pot life under ambient light. In addition, the dental photocurable composition comprising the photopolymerization initiator of the present invention has excellent bending strength.

MODES FOR CARRYING OUT THE INVENTION

In the above-mentioned photopolymerization initiator (c) of the present invention, the formula (1) of (c-3) may be an aryliodonium salt wherein R2 is an alkyl group in which 80% or more of hydrogen atoms are substituted with flourine atoms.

The present invention can be a dental photocurable composition comprising the photopolymerization initiator (c) and (a) a polymerizable monomer.

The present invention can be a dental photocurable composition comprising the photopolymerization initiator (c), (a) a polymerizable monomer, and (b) a filler.

The present invention can be a dental photocurable composition comprising
the photopolymerization initiator (c) comprising
(c-1) the photosensitizer: 0.1 to 5 parts by mass,
(c-2) the polymerization accelerator: 0.01 to 10 parts by mass, and
(c-3) the aryliodonium salt represented by the formula (1): 0.01 to 10 parts by mass,
based on 100 parts by mass of the polymerizable monomer (a).

The dental photocurable composition may comprise 10 to 1900 by weight of the filler (b), based on 100 parts by mass of the polymerizable monomer (a).

The dental photocurable composition may be a dental adhesive, a dental composite resin, a dental abutment construction material, a dental resin cement, a dental surface coating material, a dental pit fissure sealing material, and/or a dental manicure material.

Hereinafter, each of components in the dental photocurable composition of the present invention is explained in detail below.

The present invention relates to a photopolymerization initiator and a dental photocurable composition comprising the photopolymerization initiator. The dental photocurable composition of the present invention is applied for a dental adhesive, a dental composite resin, a dental abutment construction material, a dental resin cement, a dental surface covering material, a dental pit fissure sealing material, and a dental manicure material.

In clinical dentistry, in order to perform aesthetic and functional recovery for tooth defects caused by caries and fractures, after pretreatment with dental adhesives, a direct restoration with dental composite resin, and an indirect restoration performed by attaching a prosthetic device made of ceramics or hard resin using dental resin cement are performed. The dental composite resins and dental resin cements are prepared by mixing a resin matrix composed of several types of polymerizable monomers, various fillers such as inorganic fillers and organic-inorganic composite fillers, and a polymerization initiator, to obtain a uniform paste. The composite resin for dental filling is filled in the teeth in the state of an uncured paste, and after giving the anatomical morphology of the natural tooth with a dental device such as an instrument, light is applied, for example, by a dental light irradiator to cure the paste. As the irradiation light from the light irradiator, a light source having an output of about 100 to 2000 mW/cm$^2$ in the wavelength range of about 360 to 500 nm is generally used. On the other hand, the dental resin cement is used when the prosthetic device is adhered to the tooth cavity or abutment tooth, and the prosthetic device is attached to the tooth cavity or abutment tooth and then irradiated with light to be cured.

As a photopolymerization initiator for the dental composite resins and dental resin cements, a photosensitizer or a system in which a photosensitizer combined with an appropriate photopolymerization accelerator is widely used. Acylphosphine oxide compounds and α-diketone compounds are known as the photosensitizer, and in particular, the α-diketone compound has an ability to initiate polymerization in the wavelength range of visible light, which has little effect on the human body. Further, a tertiary amine compound is well known as a polymerization accelerator to be combined with the photosensitizer, a combination of the α-diketone compound and the tertiary amine compound has high polymerization activity with respect to irradiation light, and these are used in the field of dental materials. The dental photocurable composition comprising the photopolymerization initiator exhibits excellent mechanical properties such as hardness, bending strength, and compressive strength required for dental filling composite resins and dental resin cements.

However, when the combination of the α-diketone compound and the tertiary amine compound is used as the photopolymerization initiator, there arises a problem that the ambient light stability is poor. That is, the operation is performed under white light (ambient light) such as a dental light that illuminates the oral cavity or an indoor light such as a fluorescent lamp. When the combination of the α-diketone compound and the tertiary amine compound described above is used as a photopolymerization initiator, the photopolymerization initiator exhibits high sensitivity not only to irradiation light but also to ambient light, so that the curing gradually progresses during operations such as filling, building, and mounting, and there was the problem that the viscosity of the paste increases and the operation became difficult.

When the amount of the photopolymerization initiator added is reduced or the amount of the polymerization inhibitor added is increased in order to solve the above problems, the stability to ambient light is improved, but also the sensitivity to irradiation light is decreased at the same time. Therefore, a problem occurs that, even if the photopolymerization initiator is irradiated with irradiation light for a long time, sufficient curing does not proceed, the mechanical strength of the cured product is lowered, or a large amount of surface unpolymerized layer remains, so that the oral cavity is colored over time, etc. As another problem, when the tertiary amine compound is blended as a polymerization accelerator, there is the disadvantage that the cured product is easily discolored when exposed to sunlight or the like. When used as a dental adhesive, there are the problem that the adhesive strength decreases when a heat load is applied assuming the oral cavity, and the problem that the adhesive layer after curing is discolored. As described above, it has been difficult to coexist each property such as both ambient light stability and high polymerization activity to irradiation light.

As the photopolymerization initiator, a photopolymerization initiator comprising a specific aryliodonium salt, a sensitizer and an electron donor compound has been proposed, but sufficient physical properties could not be obtained. The photopolymerization initiator comprising aryliodonium salt has the following problems. First, conventional aryliodonium salts have low solubility in polymerizable monomers, and are limited to compounding at extremely low concentration due to risks such as precipitation, assuming clinical use temperature. Therefore, the photopolymerization activity was insufficient. Furthermore, there are the problem that, by using an aryliodonium salt in combination with a polymerization accelerator such as a tertiary amine compound, the photosensitivity is increased, so that the stability to ambient light is low and the operable time is significantly shortened, and the problem that the discoloration of the cured product was further promoted, when the product is exposed to sunlight.

Although the detailed promoting mechanism for discoloration is unknown, we suppose the discoloration is promoted when the cation moiety contained in the structure of the photoacid generator and the polymerization accelerator such as a tertiary amine compound or an organometallic compound form a salt or interact with each other.

However, according to the studies by the present inventors, the present inventors discovered, when a photopolymerization initiator comprising an aryliodonium salt having a specific structure is used in the dental photocurable composition, the solubility in a polymerizable monomer is increased to give no risk of precipitation and the like, an appropriate photosensitivity is exhibited, and discoloration when exposed to sunlight or the like is significantly reduced, and then completed the present invention.

As described above, the present invention provides a dental photocurable composition which exhibits high polymerization activity to irradiation light, and, for example, when applied, for example, to dental filling composite resin or dental resin cement, it has aesthetic and mechanical properties (such as hardness, bending strength, and compressive strength), and when applied as an adhesive, it has durable adhesive strength, excellent long-term storable stability, excellent ambient light stability, and excellent color tone stability.

(a) Polymerizable Monomer

The (a) polymerizable monomer which can be used in the present invention, may generally utilize the known monofunctional and/or polyfunctional polymerizable monomers without any restrictions. A representative example to be generally and preferably used is a (meth)acrylate polymerizable monomer or (meth)acrylol polymerizable monomer having an acryloyl group and/or a metacryloyl group. In addition, in the present invention, both of an acryloyl group-containing polymerizable monomer and a metacryloyl group-containing polymerizable monomer are comprehensively represented by (meth)acrylate or (meth)acryloyl.

The (meth)acrylate polymerizable monomer which can be used as the (a) polymerizable monomer is specifically illustrated as follows:

Examples of the monofunctional monomer include (meth)acrylate esters, such as methyl (meth)acrylate, ethyl (meth)acrylate, butyl (meth)acrylate (n-butyl (meth)acrylate, i-butyl (meth)acrylate), hexyl (meth)acrylate, dicyclopentyl (meth)acrylate, tetrahydrofurfuryl (meth)acrylate, 2-hydroxyethyl (meth)acrylate, glycidyl (meth)acrylate, lauryl (meth)acrylate, cyclohexyl (meth)acrylate, benzyl (meth)

acrylate, allyl (meth)acrylate, 2-ethoxyethyl (meth)acrylate, methoxy polyethylene glycol (meth)acrylate, glycerol (meth)acrylate, and isobonyl (meth)acrylate; silane compounds such as γ-(meth)acrylol oxypropyl trimethoxysilane, and γ-(meth)acrylol oxypropyl triethoxysilane; and nitrogen-containing compounds such as 2-(N,N-dimethylamino) ethyl (meth)acrylate, N-methylol (meth)acrylamide, and diacetone (meth)acrylamide.

Examples of the aromatic bifunctional monomer include 2,2-bis(4-(meth)acryloyloxy phenyl)propane, 2,2-bis(4-(3-(meth)acryloyloxy-2-hydroxypropoxy)phenyl)propane, 2,2-bis(4-(meth)acryloyloxy ethoxy phenyl)propane, 2,2-bis(4-(meth)acryloyloxydiethoxy phenyl)propane, 2,2-bis(4-(meth)acryloyloxy tetra-ethoxy phenyl)propane, 2,2-bis(4-(meth)acryloyloxypentaethoxy phenyl)propane, 2,2-bis(4-(meth)acryloyloxy diproxy phenyl)propane, 2 (4-(meth) acryloyloxy ethoxy phenyl)-2 (4-(meth) acryloyloxydiethoxy phenyl)propane, 2(4-(meth) acryloyloxy diethoxy phenyl)-2 (4-(meth) acryloyloxytriethoxy phenyl)propane, 2 (4-(meth) acryloyloxy dipropoxy phenyl)-2 (4-(meth)acryloyloxy triethoxy phenyl)propane, 2,2-bis(4-(meth)acryloyloxy diproxy phenyl)propane, and 2,2-bis(4-(meth)acryloyloxy isopropoxy phenyl)propane.

Examples of the aliphatic bifunctional monomer include 2-hydroxy-3-acryloyoxy propyl methacrylate, neopentyl glycol hydroxypivalate di(meth)acrylate, ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol di(meth)acrylate, polyethylene glycol di(meth)acrylate, 1,3-butanediol di(meth)acrylate, 1,4-butanediol di(meth)acrylate, 1,6-hexane dioldi(meth)acrylate, and glycerol di(meth) acrylate.

Examples of the trifunctional monomer include trimethylolpropanetri (meth)acrylate, trimethylolethane-tri (meth) acrylate, trimethylolmethanetri (meth)acrylate, and pentaerythritoltri (meth)acrylate.

Examples of the tetrafunctional monomer include pentaerythritoltetra (meth)acrylate, and ditrimethylolpropanetetra (meth)acrylate.

Examples of the urethane-based polymerizable monomer include di(meth)acrylate, etc., having a bifunctional, trifunctional or higher functional urethane bond and induced from an adduct of a polymerizable monomer having a hydroxyl group such as 2-hydroxyethyl(meth)acrylate, 2-hydroxypropyl (meth)acrylate, or 3-chloro-2-hydroxypropyl(meth) acrylate, and a diisocyanate compound such as methylcyclohexanediisocyanate, methylenebis(4-cyclehexylisocyanate), hexamethylenediisocyanate, trimethylhexamethylenediisocyanate, isophoronediisocyanate, diisocyanatemethylmethylbenzene, or 4,4-diphenylmethanediisocyanate.

An oligomer or prepolymer having intramolecularly at least one or more polymerizable groups other than these (meth)acrylate-based polymerizable monomers, is freely used without any restrictions. Moreover, there is no problem even when it has substituent(s) such as a fluoro group, etc. within the same molecule.

The polymerizable monomers as described above may be used alone or in a combination of a plurality of the polymerizable monomers.

The (a) polymerizable monomer (a) contained in the dental photocurable composition of the present invention may comprise a known acidic group-containing polymerizable monomer in order to impart adhesiveness to a tooth or a prosthetic device. Specific examples of the acidic group contained in the acidic group-containing polymerizable monomer include a phosphoric acid group, a carboxylic acid group, a sulfonic acid group, and a thiophosphate group, one of which is contained in the polymerizable monomer. Preferable examples of the acidic group-containing polymerizable monomer include 10-methacryloyloxydecyldihydrogen phosphate, 6-methacryloxyhexyl phosphonoacetate and 4-methacryloxyethyl trimellitate. From the viewpoint of imparting adhesiveness, the blending amount of the acidic group-containing polymerizable monomer may be 5 to 60 parts by weight, more preferably 10 to 50 parts by weight, based on 100 parts by weight of the total amount of the polymerizable monomer in the composition.

The dental photocurable composition of the present invention may comprise a silane coupling material in order to impart adhesiveness to glass ceramics. Any known silane coupling material can be used without limitation, but 3-methacryloxypropyltrimethoxysilane may be used. From the viewpoint of imparting adhesiveness, the blending amount of the silane coupling material may be 0.5 to 10 parts by weight, for example, 0.5 to 5 parts by weight, based on 100 parts by weight of the total amount of the polymerizable monomer in the composition.

(b) Filler

The filler (b) which can be used in the present invention, may be any of known fillers generally used for dental composite materials.

Types of fillers (b) include inorganic fillers, organic fillers, and organic-inorganic composite fillers, but they can used not only alone but also in combination regardless of the types of fillers.

The filler is not especially limited, and examples of the filler include silica glass, fluoroaluminosilicate glass, fluoroaluminoborosilicate glass, other silicate glass, and zirconium silicate glass containing zirconia. Among them, zirconium silicate may be used.

The above-mentioned filler (b) may be treated with a typical surface treatment material, representatively, a silane coupling material for the purpose of improving the affinity with the polymerizable monomer, the dispersibility in the polymerizable monomer, the mechanical strength of the cured product, and the water resistance. The surface treatment material and the surface treatment method are not especially limited, and known materials and methods can be adopted without limitation. The silane coupling material used for surface treatment of fillers include methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane, and hexamethyldisilazane. In addition or alteration to the silane coupling material, the surface treatment of the filler can be performed by a method using a titanate-based coupling material or an aluminate-based coupling material. The amount treated by the surface treatment material in the filler is preferably 0.01 to 30 parts by weight, more preferably 0.5 to 20 parts by weight, based on 100 parts by weight of the filler before treatment.

The shape of the filler is not especially limited, and amorphous and spherical fillers can be used. The average particle size of the filler is preferably 0.01 µm to 50 µm, more preferably 0.1 µm to 30 µm, further preferably 0.5 µm to 20 µm, and still further preferably 0.5 µm to 10 µm.

The amount of the filler (b) compounded is preferably 10 to 1900 parts by weight, more preferably 30 to 900 parts by weight, still more preferably 100 to 900 parts by weight, based on 100 parts by mass of the polymerizable monomer (a). It may be. When more than 1900 parts by weight is blended, the paste properties of the composition are hard and the composition is difficult to be handled.

(c) Photopolymerization Initiator (c-1) Photosensitizer

The photosensitizer (c-1) used in the dental photocurable composition of the present invention is not especially limited, and known compounds generally used in the dental field can be used without any restrictions.

Specific examples of the photosensitizer include α-diketones such as benzil, camphorquinone, α-naphthyl, acetonaphthone, p,p'-dimethoxybenzil, p,p'-dichlorobenzilacetyl, petanedione, 1,2-phenanthrenequinone, 1,4-phenanthrenequinone, 3,4-phenanthrenequinone, 9,10-phenanthrenequinone, and naphthoquinone; benzoinalkylethers such as benzoin, benzoinmethylether, and benzoinethylether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, p-chlorobenzophenone, and p-methoxybenzophenone; acylphosphine oxides such as 2,4,6-trimethylbenzoyldiphenyl-phosphine oxide and bis(2,6-dimethoxybenzoyl)-2,4,4-trimethylpentyl-phosphine oxide; α-aminoacetophenones such as 2-benzyl-dimethylamino-1-(4-morpholinophenyl)-butanone-1, and 2-benzyl-diethylamino-1-(4-morpholinophenyl)-propanone-1; ketals such as benzyldimethylketal, benzyldiethylketal, and benzyl (2-methoxyethylketal); and titanocenes such as bis(cyclopentadienyl)-bis(2,6-difluoro-3-(1-pyrrolyl)phenyl)-titanium, bis(cyclopentadienyl)-bis (pentanefluorophenyl-titanium, and bis(cyclopentadienyl)-bis(2,3,5,6-tetrafluro-4-disiloxyphenyl)-titanium.

The photosensitizer (c-1) to be used can be appropriately selected depending on the wavelength and intensity of the light used for the polymerization, the light irradiation time, the type and the amount of other components to be combined. In addition, the photosensitizer may be used alone or in combination of two or more. Among them, an α-diketone compound having a maximum absorption wavelength in the visible light region is preferably used, and in particular, camphorquinone may be used.

The blending amount of the photosensitizer (c-1) is usually preferably 0.01 to 5 parts by weight, more preferably 0.05 to 3 parts by weight, and further preferably 0.1 to 1 parts by weight, based on 100 parts by weight of the total amount of the polymerizable monomer. When the blending amount of the photosensitizer is less than 0.01 parts by weight, curing is insufficient because its polymerization activity again irradiation light is poor. When the photosensitizer is blended at an amount of more than 5 parts by weight, sufficient curability can be obtained but ambient light stability is shortened, and yellowish color is increased.

(c-2) Polymerization Accelerator

As the polymerization accelerator (c-2) used in the dental photocurable compositions of the present invention, known polymerization accelerators which can be generally used in the dental field may be generally used without any restrictions as long as the polymerization accelerator has polymerization accelerating ability. Tertiary amine compounds sucha as aromatic tertiary amine compounds and aliphatic tertiary amine compounds, or organometallic compounds may be used as the polymerization accelerator.

Specific examples of the above-mentioned aromatic tertiary amine compounds include N,N-dimethylaniline, N,N-diethylaniline, N,N-di-n-butylaniline, N,N-dibenzylaniline, p-N,N-dimethyl-toluidine, m-N,N-dimethyl-toluidine, p-N, N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranic acid methyl ester, N,N-dihydroxyethylaniline, p-N,N-dihydroxyethyl-toluidine, p-dimethylaminophenyl alcohol, p-dimethylaminostyrene, N,N-dimethyl-3,5-xylidine, 4-dimethylaminopyridine, N,N-dimethyl-α-naphthylamine and N,N-dimethyl-β-naphthylamine. Further, for example, the aromatic tertiary amine compounds may be p-N,N-dimethyl-toluidine, or p-N,N-dihydroxyethyl-toluidine.

Specific examples of the above-mentioned aliphatic tertiary amine compounds include tributylamine, tripropylamine, triethylamine, triethanolamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, 2-(N,N-diisopropylamino) ethyl methacrylate, 2,2'-(n)-butyl imino) diethanol, and N-[3-(dimethylamino)propryl] acrylamide and the like. Further, for example, the aliphatic tertiary amine compounds may be N,N-dimethylaminoethyl methacrylate, N,N-diethylaminoethyl methacrylate or triethanolamine.

The above-mentioned organic metal compounds are preferably an organic metal compound comprising scandium (Sc), titanium (Ti), vanadium (V), manganese (Mn), iron (Fe), cobalt (Co), nickel (Ni), copper (Cu), tin (Sn), Zinc (Zn), and/or zirconium (Zr), preferably tin (Sn), vanadium (V), and/or copper (Cu). Specific examples of the organic metal compounds comprising tin (Sn) include dibutyl-tin-diacetate, dibutyl-tin-dimaleate, dioctyl-tin-dimaleate, dioctyl-tin-dilaurate, dibutyl-tin-dilaurate, diocytl-tin-diversate, dioctyl-tin-S,S'-bis-isooctyl mercaptoacetate, and tetramethyl-1,3-diacetoxydistanoxane. Specific examples of the organic metal compounds comprising vanadium (V) include acetylacetone vanadrium, divanadium tetraoxide, vanadyl acetylacetonate, vanadium stearate oxide, vanadyl oxalate, vanadyl sulfate, oxobis(1-phenyl-1,3-butandionate) vanadium, bis(maltlate) oxovanadium, vanadium pentoxide, and sodium metavanadate. Examples of the organic metal compounds comprising copper (Cu) include copper acetylacetone, copper naphthenate, copper octylate, copper stearate and copper acetate.

The type of the polymerization accelerator (c-2) used can be appropriately selected according to the type and amount of other components to be combined. In addition, the polymerization accelerator can be used alone or in combination of two or more.

Generally, the amount of the polymerization accelerator (c-2) to be blended is preferably 0.01 to 10 parts by weight, more preferably 0.05 to 5 parts by weight, based on 100 parts by weight of the total amount of the polymerizable monomer (a). When the blending amount of the polymerization accelerator is less than 0.01 parts by weight, the polymerization promoting ability is poor and curing tends to be insufficient. When more than 10 parts by weight is blended, although it has sufficient curability, the ambient light stability is shortened and the discoloration of the cured product is increased.

(c-3) Aryliodonium Salt The aryliodonium salt (c-3) used in the dental adhesive composition of the present invention is an aryliodonium salt represented by the formula (1).
[Chemical Formula 2]

$$[(R1)_2I]^+[(R2)_bPF_{6-b}]^- \qquad (1)$$

As in the formula, aryliodonium salt consists of a cation moiety of $[(R1)_2I]^+$ and an anion moiety of $[(R2)_bPF_{6-b}]^-$. In the formula, R1 represents an organic group bonded to I, R2 represents an alkyl group in which a part of hydrogen atoms is substituted with a flourine atom, and b represents the number thereof which is an integer of from 1 to 5.

R1 in the formula (1) represents an organic group bonded to I, and R1 may be the same or different. Examples of R1 include an aryl group having 6 to 30 carbon atoms, a heterocyclic group having 4 to 30 carbon atoms, an alkyl group having 1 to 30 carbon atoms, an alkenyl group having 2 to 30 carbon atoms, and an alkynyl group having 2 to 30 carbon atoms. These may be substituted with at least one selected from the group consisting of alkyl, hydroxy, alkoxy, alkylcarbonyl, arylcarbonyl, alkoxycarbonyl, aryloxycarbonyl, arylthiocarbonyl, acrloxy, arylthio, alkylthio, aryl, heterocycle, aryloxy, alkylsulfinyl, arylsulfinyl, alkylsulfonyl, arylsulfonyl, alkyleneoxy, amino, cyano, and nitro groups and halogen.

In the above, examples of the aryl group having 6 to 30 carbon atoms include a monocyclic aryl group such as a phenyl group and a condensed polycyclic aryl group such as naphthyl, anthrasenyl, phenanthrenyl, pyrenyl, chrysenyl, naphthacenyl, benzanthrasenyl, anthraquinolyl, fluorenyl, naphthoquinone, and anthraquinone.

Examples of the heterocyclic group having 4 to 30 carbon atoms include cyclic compounds containing 1 to 3 heteroatoms such as oxygen, nitrogen and sulfur, which may be the same or different. Specific examples of the heterocyclic group include a monocyclic heterocyclic group such as thienyl, furanyl, pyranyl, pyrrolyl, oxazolyl, thiazolyl, pyridyl, pyrimidyl and pyrazinyl; and a condensed polycyclic heterocyclic group such as indrill, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thiantrenyl, phenoxadinyl, phenoxatiinyl, chromanyl, isochromanyl, dibenzothienyl, xanthonyl, thionxanthonyl and dibenzofuranyl.

Examples of the alkyl group having 1 to 30 carbon atoms include a linear alkyl group such as methyl, ethyl, propyl, butyl, hexadecyl and octadecyl; a branched alkyl group such as isopropyl, isobutyl, sec-butyl, tert-butyl, isopentyl, neopentyl, tert-pentyl and isohexyl; and a cycloalkyl group such as cyclopropyl, cyclobutyl, cyclopentyl and cyclohexyl. Examples of the alkenyl group having 2 to 30 carbon atoms include a linear or branched alkenyl group such as vinyl, allyl, 1-propenyl, isopropenyl, 1-butenyl, 2-butenyl, 3-butenyl and 1-methyl-1-propenyl. Furthermore, examples of the alkynyl group having 2 to 30 carbon atoms include a linear or branched alkynyl group such as ethynyl, 1-propynyl, 2-propynyl, 1-butynyl, 2-butynyl, 3-butynyl, 1-methyl-1-propynyl and 1-methyl-2-propynyl.

The aryl group having 6 to 30 carbons, the heterocyclic group having 4 to 30 carbons, the alkyl group having 1 to 30 carbons, the alkenyl group having 2 to 30 carbons or the alkynyl group having 2 to 30 carbons may have at least one substituent. Examples of the substituent include a linear alkyl group having 1 to 18 carbons, such as methyl, ethyl, propyl, butyl and octadecyl; a branched alkyl group having 1 to 18 carbons, such as isopropyl, isobutyl, sec-butyl, and tert-butyl; a cycloalkyl group having 3 to 18 carbons, such as cyclopropyl, cyclobutyl, cyclopentyl and cyclohexyl; a hydroxy group; a linear or branched alkoxy group having 1 to 18 carbons such as methoxy, ethoxy, propoxy, isopropoxy, butoxy, isobutoxy, sec-butoxy, tert-butoxy and dodecyloxy; a linear or branched alkylcarbonyl group having 2 to 18 carbons, such as acetyl, propionyl, butanoyl, 2-methylpropionyl, heptanoyl, 2-methylbutanoyl, 3-methylbutanoyl and octanoyl; an arylcarbonyl group having 7 to 11 carbons, such as benzoyl and naphthoyl; a linear or branched alkoxycarbonyl group having 2 to 19 carbons, such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl; an aryloxycarbonyl group having 7 to 11 carbons, such as phenoxycarbonyl and naphthoxycarbonyl; an aryl oxycarbonyl group having 7 to 11 carbons, such as phenoxycarbonyl and naphthoxycarbonyl; an arylthiocarbonyl group having 7 to 11 carbons, such as phenylthiocarbonyl and naphthoxythiocarbonyl; a linear or branched acyloxy group having 2 to 19 carbons, such as acetoxy, ehtylcarbonyloxy, propylcarbonyloxy, isobutylcarbonyloxy, sec-butylcarbonyloxy, tert-butylcarbonyloxy and octadecylcarbonyloxy; an arylthio group having 6 to 20 carbons, such as phenylthio, biphenylthio, methylphenylthio, chlorophenylthio, bromophenylthio, fluorophenylthio, hydroxyphenylthio, methoxyphenylthio, naphthylthio, 4-[4-(phenylthio)benzoyl]phenylthio, phenoxy]phenylthio, 4-[4-(phenylthio)phenoxy]phenylthio, 4-[4-(phenylthio)phenyl]phenylthio, 4-(phenylthio)phenylthio, 4-benzoylphenylthio, 4-benzoylchlorophenylthio, 4-benzoyl-methylthiophenylthio, 4-(methylthiobenzoyl)phenylthio, and 4-(p-tert-butylbenzoyl)phenylthio; a linear or branched alkylthio group having 1 to 18 carbons, such as methylthio, ethylthio, propylthio, tert-butylthio, neopentylthio and dodecylthio; an aryl group having 6 to 10 carbons, such as phenyl, tolyl, dimethylphenyl and naphthyl; a heterocyclic group having 4 to 20 carbons, such as thienyl, furanyl, pyranyl, xanthenyl, chromanyl, isochromanyl, xanthonyl, thioxanthonyl and dibenzofuranyl; an aryloxy group having 6 to 10 carbons, such as phenoxy and naphthyloxy; a linear or branched alkylsulfinyl group having 1 to 18 carbons, such as methylsulfinyl, ethylsulfinyl, propylsulfinyl, tert-pentylsulfinyl, and octylsulfinyl; an arylsulfinyl group having 6 to 10 carbons, such as phenylsulfinyl, tolyl sulfinyl and naphthyl sulfinyl; a linear or branced alkylsulfonyl group having 1 to 18 carbons, such as methylsulfonyl, ethylsulfonyl, propylsulfonyl, isopropylsulfonyl, butylsulfonyl and octylsulfonyl; an arylsulfonyl group having 6 to 10 carbons, such as phenylsulfonyl, tolyl sulfonyl (tosyl group), and naphthyl sulfonyl; an alkylene oxy group; a cyano group; a nitro group; and a halogen, such as fluorine, chlorine, bromine and iodine.

R2 in the formula (1) represents an alkyl group substituted with a flourine atom, and may have 1 to 4 carbon atoms. Specific examples of the alkyl group include a linear alkyl group such as methyl, ethyl, propyl, butyl, pentyl and octyl; a branched alkyl group such as isopropyl, isobutyl, sec-butyl and tert-butyl; and a cycloalkyl group such as cyclopropyl, cyclobutyl, cyclopentyl and cyclohexyl. R2 may be an alkyl group in which 80% or more of hydrogen atoms are substituted with fluorine atoms. Further, R2 may be an alkyl group in which 90% or more of hydrogen atoms are substituted with fluorine atoms. Furthermore, R2 may be an alkyl group in which 100% of hydrogen atoms are substituted with fluorine atoms. If the hydrogen atom in the alkyl group is not replaced by a fluorine atom, discoloration occurs after exposure to sunlight or the like.

By blending the aryliodonium salt represented by the formula (1), discoloration after exposure is suppressed and sufficient pot life under ambient light is secured. This mechanism is not bound by the specific theory of the present invention, and the followings are supposed: The introduction of the alkyl group substituted with a fluorine atom increases the hydrophobicity of the aryliodonium salt. This is also the case in the excited state, and since the interaction between the excited aryliodonium salt and the polymerization accelerator is reduced, the aryliodonium salt itself is excited or is excited by the energy obtained from the photosensitizer. At this time, since energy or electron transfer to the polymerization accelerator is suppressed, it is presumed that it leads to suppression of discoloration after exposure to sunlight and the like and securing sufficient pot life under ambient light.

Particularly preferred R2 is a linear or branched alkyl group having 1 to 4 carbon atoms and a hydrogen atom totally substituted with flourine atoms in the alkyl group, and specific examples thereof include $CF_3$, $CF_3CF_2$, $(CF_3)_2CF$, $CF_2CF_2CF_2$, $CF_3CF_2CF_2$, $(CF_3)_2CFCF_2$, $CF_3CF_2(CF_3)CF$ and $(CF_3)_3C$.

In the formula (1), the number b of R2 is an integer of from 1 to 5, preferably 2 to 4, particularly preferably 2 or 3. Each of the R2 groups present in the number of b may be the same or different.

Specific examples of the preferred anion moiety include $[(CF_3CF_2)_3PF_3]^-$, $[(CF_3CF_2CF_2)_3PF_3]^-$, $[((CF_3)_2CF)_3PF_3]^-$, $[((CF_3)_2CF)_2PF_4]^-$, $[((CF_3)_2CFCF_2)_3PF_3]^-$ and $[((CF_3)_2CFCF_2)_2PF_4]^-$.

The aryliodonium salt represented by the formula (1) has excellent solubility in a polymerizable monomer and an ability to promote polymerization. Examples of the aryliodonium salt include diphenyliodonium tris(pentafluoroethyl) trifluorophosphate, ditolyl iodonium tris(pentafluoroethyl) trifluorophosphate, bis(4-dodecylphenyl) iodonium tris(pentafluoroethyl) trifluorophosphate, bis(4-methoxyphenyl) iodonium, (4-octyloxyphenyl) phenyliodonium tris (pentafluoroethyl) trifluorophosphate, bis(4-decyloxy) phenyliodonium tris(pentafluoroethyl) trifluorophosphate, 4-(2-hydroxytetradecyloxy) phenylphenyl iodonium tris (pentafluoroethyl) trifluorophosphate, 4-isopropylphenyl (p-tolyl) iodonium tris(pentafluoroethyl) trifluorophosphate, 4-isobutylphenyl (p-tolyl)iodonium tris(pentafluoroethyl) trifluorophosphate, bis(4-tert-butylphenyl) iodonium tris (pentafluoroethyl) trifluorophosphate and bis(4-tert-butylphenyl) iodonium tris(pentafluoropropyl) trifluorophosphate.

Generally, the blending amount of the aryliodonium salt (c-3) is preferably 0.01 to 10 parts by weight, more preferably 0.05 to 5 parts by weight, or more preferably 0.05 to 5 parts by weight, and, for example, may be 0.5 to 3 parts by weight, based on 100 parts by weight of the total amount of (a) polymerizable monomer. When the blending amound of the aryliodonium salt is less than 0.01 parts by weight, the polymerization promoting ability is poor and the curing becomes insufficient. When more than 10 parts by weight is blended, although it has sufficient curability, the ambient light stability becomes short and the cured product becomes brownish and discoloration increases.

The photopolymerization initiators can be used alone or in combination of two or more. Further, the polymerization initiators may be, with no problem, subjected to a secondary treatment such as being encapsulated in microcapsules as necessary. Further, the various types of photopolymerization initiators can be used alone or in combination of two or more, regardless of the polymerization mode or polymerization method.

In addition to the photopolymerization initiator (c), a chemical polymerization initiator may be blended in the dental photocurable composition of the present invention, and known chemical polymerization initiators can be used without limitation. Examples of the chemical polymerization initiator include a thiourea derivative, an organic peroxide having a hydroperoxide group and a sulfinate, which can be used alone or in combination.

As the thiourea derivative, any known thiourea derivative can be used without limitation. Specific examples of thiourea derivatives include dimethylthiourea, diethylthiourea, tetramethylthiourea, (2-pyridyl) thiourea, N-methylthiourea, ethylenethiourea, N-allyl thiourea, and N-allyl-N'-(2-hydroxyethyl)thiourea, N-benzyl thiourea, 1,3dicyclohexylthiourea, N,N'-diphenylthiourea, 1,3-di(p-tolyl) thiourea, 1-methyl-3-phenylthiourea, Examples thereof include N-acetylthiourea, N-benzoylthiourea, diphenylthiourea and dicyclohexylthiourea. Among these, N-acetylthiourea and N-benzoylthiourea. A plurality of types of the thiourea derivative may be used in combination, if necessary. The blending amount of the thiourea derivative is preferably 0.1 to 4 parts by weight, based on the total amount of the total polymerizable monmoer. When the blending amount is less than 0.1 part by weight, the polymerization promoting ability is insufficient, and when it exceeds 4 parts by weight, the storage stability may be decreased.

As the organic peroxide having a hydroperoxide group, any known organic peroxide having a hydroperoxide group can be used without limitation. Specific examples of the organic peroxides include t-butyl hydroperoxide, cyclohexyl hydroperoxide, cumene hydroperoxide, diisopropylbenzene hydroperoxide, p-mentan hydroperoxide, diisopropylbenzene hydroperoxide, 1,1,3,3-tetramethylbutyl hydroperoxide, and cumene hydroperoxide, which may be used from the viewpoint of reactivity. A plurality of types of these organic peroxides may be used in combination, if necessary. The blending amount of the organic peroxide having a hydroperoxide group is preferably 0.1 to 4 parts by weight, based on the total amount of the total polymerizable monomer. When the blending amount is less than 0.1 part by weight, the ability as a polymerization accelerator is insufficient, and when it exceeds 4 parts by weight, the storage stability may decrease.

Examples of the sulfinic acid derivative include salts of p-toluenesulfinic acid, benzenesulfinic acid, 2,4,6-trimethylbenzenesulfinic acid, 2,4,6-triethylbenzenesulfinic acid, and 2,4,6-triisopropylbenzenesulfinic acid (which may be a salt of alkali metals of alkaline earth metals). Specific examples of the sulfinic acid salt compound include sodium p-toluenesulfinate and sodium benzenesulfinate.

(d) Solvent

The solvent (d) used in the present invetnion can be used without any restrictions as long as it is a known solvent used in the dental field. Examples of representative solvent preferably used include water and organic solvents. Among the organic solvents, a water-soluble volatile organic solvent having a boiling point of 100° C. or less under normal pressure are preferable, and specific examples thereof include ethanol, methanol, 1-propanol, isopropyl alcohol, acetone, methyl ethyl ketone, 1,2-dimethoxyethane, 1,2-diethoxyethane and tetrahydrofuran. Water, acetone and ethanol are particularly preferable. The amount of the solvent (d) blended may be 1 to 300 parts by weight, for example, 50 to 300 parts by weight, or 100 to 250 parts by weight, based on the total amount of the polymerizable monomer.

Other Components

Further, the dental photocurable composition of the present invention may contain components other than the above-mentioned components (a) to (d) as long as the effects of the present invention are not impaired. For example, excipients typified by fumed silica; benzophenone-based and benzotriazole-based ultraviolet absorvers; polymerization inhibitors such as hydroquinone, hydroquinone monomethyl ether and 2,5-ditert-butyl-4-methylphenol; chain transfer agents, for example, an α-alkylstyrene compounds; mercaptan compounds such as n-butyl mercaptane and n-octyl mercaptane; terpenoid compounds such as limonene, milsen, α-terpinene, β-terpinene, γ-terpenine, terpenine, β-pinene and α-pinene; metal scavengers such as an aminocarboxylic acid-based chelating agent and a phosphonic acid-based chelating agent, discoloration inhibitors, antibacterial agents, coloring pigments, water and solvents which can be mixed with water in any ratio, and other conventionally known additives can be arbitrarily added, if necessary.

The method for producing the dental photocurable composition of the present invnetion is not especially limited. A general method for producing a dental photocurable composition, comprises mixing the polymerizable monomer (a) and the photopolymerization initiator (c) in advance to give a binder resin, mixing the binder resin with the filler (b), then kneading the mixture and removing air bubbles under vacuum to produce a uniform paste-like composition; or mixing the polymerizable monomer (a) with the photopolymerization initiator (c) and the solvent (d) to produce a homogeneous liquid compositon. Also in the present invention, the dental photocurable composition can be produced by the above-mentioned production method without any problem.

INDUSTRIAL APPLICABILITY

The dental photocurable composition is used for oral treatment in the dental field, and is applied for dental adhesives, dental composite resins, dental abutment constructions materials, dental resin cements, and dental surface coatings, dental pit fissure sealing materials, and dental manicure materials. Accordingly, the dental photocurable composition can be for industrial use.

EXAMPLES

Examples of the present invention will be specifically described below, but the present invention is not limited to these examples.

The materials used in Examples and Comparative Examples and their abbreviations are shown below.

(A) Polymerizable Monomer

Bis-GMA: 2,2-Bis[4-(3-methacryloyloxy-2-hydroxy-propoxy)-phenyl]propane
2.6E: 2,2-Bis(4-(meth)acryloyloxypolyethoxyphenyl) propane having an average ethoxy group addition mole of 2.6
UDMA: N,N-(2,2,4-trimethylhexamethylene) bis [2-(aminocarboxy)ethanol]methacrylate
TEGDMA: Triethylene glycol dimethacrylate
GDMA: Glycerol dimethacrylate
2-HEMA: 2-Hydroxyethyl methacrylate
MDP: 10-Methacryloyloxydecyldihydrogen phosphate
6-MHPA: 6-Methacryloxyhexyl phosphonoacetate
4-MET: 4-Methacryloxyethyl trimellitic acid (C) Polymerization Initiator (c-1) Photosensitizer
CQ: α-Camphorquinone
(c-2) Polymerization Accelerator
Aromatic Tertiary Amine Compounds
DMBE: Ethyl N,N-dimethylaminobenzoate
Aliphatic Tertiary Amine Compound
DMAEMA: N,N-Dimethylaminoethyl methacrylate
Organometallic compounds
SnL: Dioctyl-tin-dilaurate
(c-3) Diaryliodonium Salt
IPIFP: 4-Isopropylphenyl (p-tolyl) iodonium tris(pentafluoroethyl) trifluorophosphate

[Chemical Formula 3]

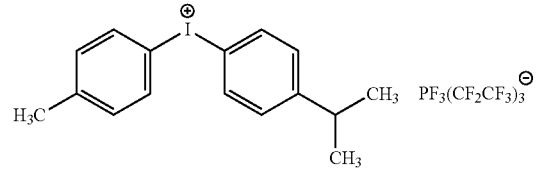

tBIFP: Bis(4-tert-butylphenyl) iodonium tris(penta-fluoropropyl) trifluorophosphate

[Chemical Formula 4]

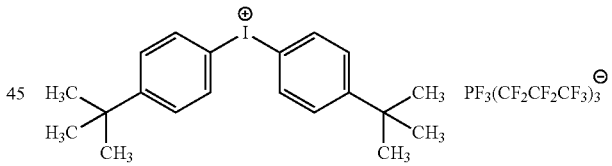

DPIHP: Diphenyliodonium hexafluorophosphate
(d) Solvent
Water
Acetone (B) Filler The method for producing each filler used in the preparation of the dental photocurable composition is shown below.

To 100.0 g of zirconium silicate filler (average particle size 2.2 μm: zironia 90 wt %, silica 10 wt %) was added a silane coupling treatment liquid obtained by stirring 50.0 g of water, 35.0 g of ethanol, and 3.0 g of 3-methacryloyloxy-propyltrimehoxysilane as a silane coupling material at room temperature for 2 hours, and the mixture was stirred and mixed for 30 minutes. Then, heat treatment was performed at 140° C. for 15 hours to obtain Filler 1.

100.0 g of zirconium silicate filler (average particle size 0.8 μm: zirconia 85 wt %, silica 15 wt %) was added a silane coupling treatment liquid obrained by stirring 50.0 g of water, 35.0 g of ethanol, and 5.0 g of 3-methacryloyloxy-propyltrimethoxysilane as a silane coupling material at room temperature for 2 hours, and the mixture was stirred and mixed for 30 minutes. Then, heat treatment was performed at 140° C. for 15 hours to obtain Filler 2.

Chemical Polymerization Initiators
Thiourea Derivative
BTU: N-benzoylthiourea
Organic Peroxides Having Hydroperoxide Group
CHP: Cumene hydroperoxide
UV Absorber
BT: 2-(2-Hydroxy-5-methylphenyl) benzotriazole
Polymerization Inhibitor
BHT: 2,6-di-t-butyl-4-methylphenol Production Method of Dental Photocurable Composition (Composite Resin for Dental Filling)

The polymerizable monomer (a), the polymerization initiator (c), and others shown in Table 1 were mixed using a mix rotor VMRC-5 at 100 rpm for 24 hours to obtain a binder resin in which each material was uniformly dissolved. Then, the binder resin and the filler (b) are put into a kneader, stirred uniformly, and then defoamed under vacuum to prepare dental photurable compositions of Examples 1 to 12 and Comparative Examples 1 and 2.

TABLE 1

|  | (a) Polymerizable mononer | (b) Filler | (c) Polymerization initiator ||||||| Others ||
|  |  |  | (c-1) Photo-sensitizer | (c-2) Polymerization accelerator ||| (c-3) Aryl-iodonium salt | Other Aryl-iodonium salt | Polymerization inhibitor | UV absorber |
|  |  |  |  | Aromatic amine | Aliphatic amine | Organo-metallic compound |  |  |  |  |
| Ex. 1 | Bis-GMA/TEGDMA = 60/40 | Filler 1 (250) | CQ (0.4) | DMBE (0.5) |  |  | IPIFP (0.5) |  | BHT (0.05) | BT (0.005) |
| Ex. 2 | Bis-GMA/TEGDMA = 60/40 | Filler 1 (300) | CQ (0.4) | DMBE (0.5) | DMAEMA (0.5) |  | IPIFP (0.5) |  | BHT (0.05) | BT (0.005) |
| Ex. 3 | Bis-GMA/TEGDMA = 60/40 | Filler 1 (300) | CQ (0.4) |  | DMAEMA (1.0) |  | IPIFP (0.5) |  | BHT (0.05) | BT (0.005) |
| Ex. 4 | Bis-GMA/TEGDMA = 60/40 | Filler 1 (250) | CQ (0.4) | DMBE (0.5) |  |  | tBIFP (0.5) |  | BHT (0.05) | BT (0.005) |
| Ex. 5 | Bis-GMA/TEGDMA = 60/40 | Filler 2 (300) | CQ (0.4) | DMBE (0.5) |  |  | IPIFP (3) |  | BHT (0.05) | BT (0.005) |
| Ex. 6 | Bis-GMA/TEGDMA = 60/40 | Filler 1 (250) | CQ (1.5) | DMBE (0.5) |  |  | IPIFP (0.5) |  | BHT (0.05) | BT (0.005) |
| Ex. 7 | Bis-GMA/TEGDMA = 60/40 | Filler 1 (250) | CQ (0.4) | DMBE (2.0) |  |  | IPIFP (0.5) |  | BHT (0.05) | BT (0.005) |
| Ex. 8 | Bis-GMA/TEGDMA = 60/40 | Filler 2 (300) | CQ (0.3) | DMBE (0.5) |  |  | IPIFP (0.5) |  | BHT (0.05) | BT (0.005) |
| Ex. 9 | Bis-GMA/TEGDMA = 60/40 | Filler 1 (250) | CQ (0.4) |  |  | SnL (0.5) | tRIFP (0.2) |  | BHT (0.05) | BT (0.005) |
| Ex. 10 | Bis-GMA/TEGDMA/MDP = 60/20/20 | Filler 1 (250) | CQ (0.4) | DMBE (0.5) |  |  | IPIFP (0.5) |  | BHT (0.05) | BT (0.005) |
| Ex. 11 | Bis-GMA/TEGDMA = 60/40 | Filler 1 (250) | CQ (0.4) | DMBE (0.5) |  |  | IPIFP (5) |  | BHT (0.05) | BT (0.005) |
| Ex. 12 | Bis-GMA/TEGDMA = 60/40 | Filler 1 (250) | CQ (0.4) | DMBE (0.5) |  |  | IPIFP (0.05) |  | BHT (0.05) | BT (0.005) |
| Com. Ex. 1 | Bis-GMA/TEGDMA = 60/40 | Filler 1 (250) | CQ (0.4) | DMBE (0.5) |  |  |  | DPIHP (0.5) | BHT (0.05) | BT (0.005) |
| Com. Ex. 2 | Bis-GMA/TEGDMA = 60/40 | Filler 1 (250) | CQ (0.4) | DMBE (0.5) |  |  |  | DPIHP (0.1) | BHT (0.05) | BT (0.005) |

Production Method of Dental Photocurable Composition (Dental Resin Cement)

The polymerizable monomer (a), the polymerization initiator (c), and others shown in Table 2 were mixed using a mix rotor VMRC-5 at 100 rpm for 24 hours to obtain a binder resin in which each material was uniformly dissolved. Obtained. Then, the binder resin and the filler (b) were put into a kneader, stirred uniformly, defoamed under vacuum to obtain Pastes 1 and 2, and then filled in a double syringe (5 mL) manufactured by Mixpack, to prepare dental photocurable compositions of Examples 13 to 22 and Comparative Examples 3 to 4.

TABLE 2

| | | (a) Polymerizable monomer | (b) Filler | (c) Polymerization initiator | | | | | Chemical polymerization initiator | | Others | |
|---|---|---|---|---|---|---|---|---|---|---|---|---|
| | | | | (c-1) Photo-sensi-tizer | (c-2) Polymerization accelerator | | | (c-3) Diaryl-io-donium salt | Thiourea deriva-tive | Organic perox-ides having hydro-peroxide group | Other Arylio-donium salt | Poly-meri-zation in-hibitor | UV ab-sorber |
| | | | | | Aro-matic amine | Ali-phatic amine | Organo-metallic com-pound | | | | | | |
| Ex. 13 | Paste 1 | 2.6E/UDMA/TEGDMA/ MDP = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | DMBE (1.2) | | | IPIFP (1.0) | | CHP (1.0) | | BHT (0.1) | |
| Ex. 14 | Paste 1 | 2.6E/UDMA/TEGDMA/ 6-MHPA = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (150) | | DMBE (0.6) | DMAEMA (0.5) | | tBIFP (0.8) | | CHP (1.0) | | BHT (0.1) | |
| Ex. 15 | Paste 1 | 2.6E/UDMA/TEGDMA/ MDP = 40/20/20/20 | Filler 2 (150) | CQ (0.5) | | | | | BTU (1.0) | | | | BT (0.01) |
| | Paste 2 | 2.6E/UDMA/ TEGDMA = 40/20/40 | Filler 2 (200) | | | DMAEMA (1.5) | | IPIFP (1.0) | | CHP (1.0) | | BHT (0.1) | |
| Ex. 16 | Paste 1 | 2.6E/UDMA/TEGDMA/ MDP = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | DMBE (1.2) | | | IPIFP (6.0) | | CHP (1.0) | | BHT (0.1) | |
| Ex. 17 | Paste 1 | 2.6E/UDMA/TEGDMA/ MDP = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | DMBE (1.2) | | | IPIFP (0.5) | | CHP (1.0) | | BHT (0.1) | |
| Ex. 18 | Paste 1 | 2.6E/UDMA/TEGDMA/ 6-MHPA = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | DMBE (1.2) | | | tBIFP (0.4) | | CHP (1.0) | | BHT (0.1) | |
| Ex. 19 | Paste 1 | 2.6E/UDMA/TEGDMA/ MDP = 40/20/20/20 | Filler 2 (200) | CQ (1.2) | | | | | BTU (1.0) | | | | BT (0.01) |
| | Paste 2 | 2.6E/UDMA/ TEGDMA = 40/20/40 | Filler 2 (200) | | DMBE (1.2) | | | IPIFP (1.0) | | CHP (1.0) | | BHT (0.1) | |
| Ex. 20 | Paste 1 | 2.6E/UDMA/ TEGDMA = 40/20/40 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | | | SnL (0.5) | IPIFP (1.0) | | CHP (1.0) | | BHT (0.1) | |
| Ex. 21 | Paste 1 | 2.6E/UDMA/TEGDMA/ MDP = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | DMBE (1.2) | | | IPIFP (10) | | CHP (1.0) | | BHT (0.1) | |
| Ex. 22 | Paste 1 | 2.6E/UDMA/TEGDMA/ MDP = 40/20/20/20 | Filler 2 (200) | CQ (0.5) | | | | | BTU (1.0) | | | | BT (0.01) |
| | Paste 2 | 2.6E/UDMA/ TEGDMA = 40/20/40 | Filler 2 (200) | | DMBE (1.2) | | | IPIFP (0.1) | | CHP (1.0) | | BHT (0.1) | |

TABLE 2-continued

| | (a) Polymerizable monomer | (b) Filler | (c) Polymerization initiator | | | | | Chemical polymerization initiator | | | | |
|---|---|---|---|---|---|---|---|---|---|---|---|---|
| | | | (c-1) Photo-sensitizer | (c-2) Polymerization accelerator | | | (c-3) Diaryl-iodonium salt | Organic perox-ides | Others | | | |
| | | | | Aro-matic amine | Ali-phatic amine | Organo-metallic com-pound | | Thiourea deriva-tive | having hydro-peroxide group | Other Arylio-donium salt | Poly-meri-zation in-hibitor | UV ab-sorber |
| Com. Ex. 3 | Paste 1  2.6E/UDMA/TEGDMA/ MDP = 40/20/20/20 | Filler 2 (200) | CQ (0.5) | | | | | BTU (1.0) | | | | BT (0.01) |
| | Paste 2  2.6E/UDMA/ TEGDMA = 40/20/40 | Filler 2 (200) | | DMBE (1.2) | | | | | CHP (1.0) | DPIHP (0.5) | BHT (0.1) | |
| Com. Ex. 4 | Paste 1  2.6E/UDMA/TEGDMA/ MDP = 40/20/20/20 | Filler 2 (200) | CQ (0.5) | | | | | BTU (1.0) | | | | BT (0.01) |
| | Paste 2  2.6E/UDMA/ TEGDMA = 40/20/40 | Filler 2 (200) | | DMBE (1.2) | | | | | CHP (1.0) | DPIHP (0.1) | BHT (0.1) | |

Production Method of Dental Photocurable Composition

The polymerizable monomer (a), the polymerization initiator (c), and others shown in Table 3 were mixed using a mix rotor VMRC-5 at 100 rpm for 24 hours, to prepare dental photocurable compositions of Example 23 to 28 and Comparative Examples 5 to 8 in which each material was uniformly dissolved.

Production Method of Dental Photocurable Composition (Dental Adhesive)

(a) Polymerizable monomer, (c) photopolymerization initiator and (d) solvent shown in Table 4 were mixed using a Turbula mixer T2F (manufactured by Shinmaru Enterprises Corp.) to prepare a homogeneous liquid dental photocurable composition, and filled in a light-shielding plastic container

TABLE 3

| | (a) Polymerizable monomer | (c) Polymerization initiator | | | | | Others |
|---|---|---|---|---|---|---|---|
| | | (c-1) Photo-sensitizer | (c-2) Polymerization accelerator | | | (c-3) Aryl-iodonium salt | Other Aryl-iodonium salt |
| | | | Aromatic amine | Aliphatic amine | Organo-metallic compound | | |
| Ex. 23 | Bis-GMA/TEGDMA = 60/40 | CQ (0.4) | DMBE (0.5) | | | IPIFP (0.5) | |
| Ex. 24 | Bis-GMA/TEGDMA = 60/40 | CQ (0.4) | DMBE (0.5) | DMAEMA (0.5) | | IPIFP (0.5) | |
| Ex. 25 | Bis-GMA/TEGDMA = 60/40 | CQ (0.4) | | DMAEMA (1.0) | | IPIFP (0.5) | |
| Ex. 26 | Bis-GMA/TEGDMA = 60/40 | CQ (0.4) | DMBE (0.5) | | | tBIFP (0.5) | |
| Ex. 27 | Bis-GMA/TEGDMA = 60/40 | CQ (0.4) | DMBE (0.5) | | | IPIFP (3) | |
| Ex. 28 | Bis-GMA/TEGDMA = 60/40 | CQ (0.2) | | | SnL (1.0) | IPIFP (0.5) | |
| Com. Ex. 5 | Bis-GMA/TEGDMA = 60/40 | CQ (0.4) | DMBE (0.5) | | | | DPIHP (0.5) |
| Com. Ex. 6 | Bis-GMA/TEGDMA = 60/40 | CQ (0.4) | DMBE (0.5) | | | | DPIHP (0.1) |
| Com. Ex. 7 | Bis-GMA/TEGDMA = 60/40 | CQ (0.4) | | | | | |
| Com. Ex. 8 | Bis-GMA/TEGDMA = 60/40 | CQ (0.4) | DMBE (0.5) | | | | | to prepare dental photocurable compositions of Examples 29 to 36 and Comparative Examples 9 to 10.

TABLE 4

| | (a) Polymerizable monomer | | (c) Polymerization initiator | | | | | Others | |
|---|---|---|---|---|---|---|---|---|---|
| | (a) Polymerizable monomer | (a) Acid group-containing polymerizable monomer | (c-1) Photo-sensitizer | (c-2) Polymerization accelerator | | (c-3) Aryl-iodonium salt | (d) Solvent | Other Aryl-iodonium salt | Poly-merization inhibitor |
| | | | | Aromatic amine | Aliphatic amine | | | | |
| Ex. 29 | Bis-GMA/TEGDMA = 60/30 | MDP (10) | CQ (0.4) | DMBE (0.5) | | IPIFP (0.5) | Acetone/water = 200/100 | | BHT (0.01) |
| Ex. 30 | Bis-GMA/TEGDMA = 50/30 | MDP (20) | CQ (0.2) | DMBE (0.3) | DMAEMA (0.3) | IPIFP (0.5) | Acetone/water = 150/100 | | BHT (0.01) |
| Ex. 31 | Bis-GMA/2-HEMA = 50/30 | MDP (20) | CQ (0.4) | | DMAEMA (0.8) | IPIFP (0.3) | Acetone/water = 150/50 | | BHT (0.01) |
| Ex. 32 | Bis-GMA/TEGDMA = 60/30 | 6-MHPA (10) | CQ (0.4) | DMBE (1.5) | | IPIFP (0.5) | Acetone/water = 75/25 | | BHT (0.01) |
| Ex. 33 | Bis-GMA/TEGDMA = 50/30 | MDP (20) | CQ (1.0) | DMBE (0.5) | | IPIFP (3) | Acetone/water = 150/50 | | BHT (0.01) |
| Ex. 34 | Bis-GMA/2-HEMA = 40/20 | MDP (40) | CQ (0.4) | DMBE (0.5) | | IPIFP (3) | Acetone/water = 150/50 | | BHT (0.01) |
| Ex. 35 | Bis-GMA/2-HEMA = 40/20 | MDP/4-MET = 20/20 | CQ (0.4) | DMBE (0.5) | | IPIFP (1) | Acetone/water = 150/50 | | BHT (0.01) |
| Ex. 36 | Bis-GMA/GDMA/2-HEMA = 40/10/10 | MDP/4-MET = 20/20 | CQ (0.4) | DMBE (0.5) | | IPIFP (1) | Acetone/water = 150/50 | | BHT (0.01) |
| Com. Ex. 9 | Bis-GMA/TEGDMA = 50/30 | MDP (20) | CQ (0.4) | DMBE (0.5) | | IPIFP (1) | Acetone/water = 150/50 | DPIHP (0.5) | BHT (0.01) |
| Com. Ex. 10 | Bis-GMA/TEGDMA = 50/30 | MDP (20) | CQ (0.4) | DMBE (0.5) | | | Acetone/water = 150/50 | DPIHP (0.1) | BHT (0.01) |

Test methods adopted in Examples and Comparative Examples are as follows. The composite resin for dental filling and the dental resin composition were directly collected, and the dental resin cement was a paste obtained by mixing Pastes 1 and 2 using a mixing chip manufactured by Mixpac AG.

(1) Bending Strength

The prepared dental photocurable composition was filled into a stainless steel mold, cover glasses were put on both sides, press-weld with a glass kneading plate, and then light irradiation was performed at 5 locations for 10 seconds each by using a photopolymerization irradiator (Blue Shot manufactured by Shofu Inc.) to cure the curable composition. After curing, the cured product was taken out from the mold, and then the back surface was also irradiated with light in the same manner to prepare a test piece (25×2×2 mm: rectangular parellelepiped shape). The test piece was immersed in water at 37° C. for 24 hours, and then a bending test was performed.

The bending test was performed using an Instron universal testing machine (manufactured by Instron Corp.) at a distance between fulcrums of 20 mm and a crosshead speed of 1 mm/min.

(2) Ambient Light Stability

The height of the dental lamp (Luna-Vue S manufactured by Morita Manufacturing Co., Ltd.) was adjusted by using an illuminometer so that a sample installation section is exposed to light having an illuminance of 8000±1000 lx. After placing a slide glass (26×16 mm, thickness 2 mm) on a glass kneading plate lined with matte black paper, a sample of about 30 mg was collected on the slide glass. After exposing the sample to lingt on the sample installation section for 60±5 seconds, the sample was taken out from the sample installation section and immediately pressed against another slide glass to form a thin layer. If the state of the sample at this time was not physically uniform, it was determined that curing had started, and the time unitl curing was evaluated in 5-second increments. The longer this time is, the better the ambient light stability is.

(3) Discoloration of Cured Product a) Dental Photocurable Composition (Excluding Dental Adhesives)

After filling each of the prepared dental photocurable compositions into a stainless steel mold (15φ×1 mm: disk shape), a cover glass was placed from above and pressure-welded using a glass plate. Light irradiation was performed for 1 minute from the cover glass using a photopolymerization irradiator (Grip Light II manufactured by Shofu Inc.) to cure the dental photocurable composition, and after removing the cured product from the mold, the cover glass is removed and the color tone of this test piece was measured.

The color measurement was performed by placing the test piece on the background of a standard white plate (D65/10° X=81.07, Y=86.15, Z=93.38) and using a spectrocolorimeter (manufactured by BYK Chemie Corp.) under a given constant condition (light source: C, viewing angle: 2°, measurement area: 11 mm). Then, after exposing the test piece to light for 24 hours with a xenon lamp light exposure tester (Suntest CPS+), the color tone of the test piece was measured again, and the difference in discoloration was expressed by ΔE calculated from the following formula.

$$\Delta E = \{(\Delta L^*)^2 (\Delta a^*)^2 (\Delta b^*)^2\}^{1/2}$$

$$\Delta L^* = L1^* - L2^*$$

$$\Delta a^* = a1^* - a2^*$$

$$\Delta b^* = b1^* - b2^*$$

wherein L1* is a brightness index before light exposure,
L2* is a brightness index after light exposure,
a1* and b1* are color quality indexes before light exposure,
and a2* and b2* are color quality indexes after light exposure b) Dental Photocurable Compostion (Dental Adhesive)

A 50 μm-thick polyethylene frame was fixed on a glass plate, the prepared dental photocurable composition was applied into the frame, and air drying was repeated until the liquid level stopped moving, resulting in a thickness of 50 μm or more. The glass plate was pressure-welded and irradiated with light for 1 minute using a photopolymerization irradiator (Grip Light II manufactured by Shofu Inc.) to cure the dental curable composition. After taking out the cured product from the frame, the cover glass was removed and color tone of the test piece was measured. The color measurement was measured by placing the test piece on the background of a standard white plate (D65/10° X=81.07, Y=86.15, Z=93.38) and using a spectrocolorimeter (manufactured by BYK Chemie Corp.) under given conditions (light source: C, viewing angle: 2°, measurement area: 11 mm). Then, the test piece was immersed in water at 37° C. for 2 months, the color tone of the test piece was measured again, and the difference in discoloration was represented by ΔE calculated from the following formula.

$$\Delta E = \{(\Delta L^*)^2 (\Delta a^*)^2 (\Delta b^*)^2\}^{1/2}$$

$$\Delta L^* = L1^* - L2^*$$

$$\Delta a^* = a1^* - a2^*$$

$$\Delta b^* = b1^* - b2^*$$

wherein L1* is a brightness index before immersion,
L2* is a brightness index after immersion,
a1* and b1* are color quality indexes before immersion, and
a2* and b2* are color quality indexes after immersion.

(4) Evaluation of Storage Stability

The prepared dental photocurable composition was stored under a shield in an incubator set at 50° C., and after 90 days, a test equivalent to (3) discoloration of cured product was performed and precipitation of aryliodonium salt were confirmed. Storage stability was evaluated from the changes over time between the initial value and the value after 90 days at 50° C. For precipitation, the paste was discharged from the syringe and the presence or absence of precipitation was confirmed. The one having no precipitation was designated as A, the one having slight precipitation was designated as B, and the one having obvious precipitation was designated as C. For each composition, a dental photocurable composition from which the aryliodonium salt was removed was prepared as a reference sample, and it was confirmed that all of them had no precipitate.

(5) Evaluation of Durable Adhesive Strength

A crown of extracted bovine mandibular permanent central incisor was cut, and the bovine tooth fragment was embedded with an epoxy resin. The embedded bovine tooth was used with pouring water, and the dentin is exposed with #600 water-resistant abrasive paper, washed with water, and dried.

A double-sided tape with a hole having a diameter of 4 mm was applied to the exposed dentin to define the adhesive surface. A plastic mold (inner diameter 4 mm, height 2 mm or 4 mm) was fixed to the defined surface. A dental curable composition was applied to the adhesive surface, and cured by irradiation of light for 20 seconds by a photopolymerization irradiator (Grip Light II manufactured by Shofu Inc.). After that, the dental composite resin "BEAUTIFL Flow Plus" (Shofu Inc.) was filled in the mold, and light irradiation was performed again for 20 seconds to cure. The plastic mold was removed to prepare an adhesive test piece. After immersing this adhesive test piece in 37° C. distilled water for 24 hours, by using an Instron universal testing machine (Instron 5567, manufactured by Instron Corp.) at a crosshead speed of 1 mm/min. a dentin adhesiveness test due to shear adhesion strength was conducted and an initial adhesive strength was measured.

In addition, an adhesion test piece was prepared and immersed in 37° C. distilled water for 24 hours, and then subjected to 10,000 thermal cycles (alternately immersed at 55° C./30 seconds and 5° C./30 seconds) to perform a dentin adhesion test. The result was a durable adhesive strength.

Examples 1 to 12

The dental photocurable compositions of Examples 1 to 12 showed high bending strength, excellent ambient light stability, and high discoloration resistance, and even after 90 days at 50° C., deterioration of discloration resistance and precipitation were not almost observed. The compositions have excellent storage stability.

Comparative Examples 1 and 2

The dental photocurable composition of Comparative Example 1 had low ambient light stability and remarkable discoloration, and precipitation of an aryliodonium salt was observed. It was confirmed that the dental photocurable composition of Comparative Example 2 had low bending strength and large discoloration.

Table 5 shows the evaluation results of the dental photocurable compositions (dental resin cement) of Examples 1-12 and Comparative Examples 1 and 2.

TABLE 5

| | Ambient | | | Storage stability | |
| --- | --- | --- | --- | --- | --- |
| | Bending strength (MPa) | light stability (sec) | Discoloration ΔE | Discoloration ΔE | Precipitation |
| Ex. 1 | 122 | 90 | 2.2 | 3.3 | A |
| Ex. 2 | 123 | 90 | 3 | 2 | A |
| Ex. 3 | 118 | 70 | 3.4 | 2.5 | A |
| Ex. 4 | 111 | 90 | 2.3 | 3 | A |
| Ex. 5 | 143 | 75 | 5 | 6.4 | A |
| Ex. 6 | 123 | 65 | 3.4 | 3 | A |
| Ex. 7 | 134 | 65 | 4.6 | 4.2 | A |
| Ex. 8 | 144 | 90 | 1.2 | 1.4 | A |
| Ex. 9 | 142 | 70 | 4 | 3.8 | A |
| Ex. 10 | 115 | 100 | 3.2 | 3.1 | A |
| Ex. 11 | 152 | 60 | 4.5 | 4.5 | A |
| Ex. 12 | 103 | 120 | 1.2 | 0.8 | A |
| Com. Ex. 1 | 83 | 15 | 10.5 | 12 | C |
| Com. Ex. 2 | 55 | 55 | 7.7 | 6.4 | B |

Examples 13 to 22

The dental photocurable compositions of Examples 13 to 22 showed high bending strength, excellent ambient light stability, and high discoloration resistance, and even after 90 days at 50° C., deterioration of discoloration resistance and precipitation were not almost observed. The dental photocurable compositions had excellent storage stability.

Comparative Examples 3 to 4

The dental photocurable composition of Comparative Example 3 was markedly discolored, and precipitation of an aryliodonium salt was observed. It was confirmed that the dental photocurable composition of Comparative Example 4 had low bending strength and large discoloration.

Table 6 shows the evaluation results of the dental photocurable compositions of Examples 13 to 22 and Comparative Examples 3 and 4.

TABLE 6

|  | Bending strength (MPa) | Ambient light stability (sec) | Discoloration $\Delta E$ | Storage stability Discoloration $\Delta E$ | Precipitation |
|---|---|---|---|---|---|
| Ex. 13 | 144 | 80 | 2.8 | 3.5 | A |
| Ex. 14 | 123 | 95 | 3.3 | 2.8 | A |
| Ex. 15 | 115 | 90 | 3.1 | 3.4 | A |
| Ex. 16 | 136 | 60 | 4.5 | 4.7 | A |
| Ex. 17 | 140 | 85 | 1.1 | 0.8 | A |
| Ex. 18 | 142 | 90 | 1.8 | 0.6 | A |
| Ex. 19 | 133 | 60 | 3.8 | 3.5 | A |
| Ex. 20 | 133 | 90 | 2.1 | 1.5 | A |
| Ex. 21 | 144 | 60 | 4.7 | 4.6 | A |
| Ex. 22 | 105 | 100 | 2.4 | 3.1 | A |
| Com. Ex. 3 | 91 | 50 | 5.5 | 7.2 | C |
| Com. Ex. 4 | 81 | 90 | 10 | 9.8 | B |

Examples 23 to 28

The dental photocurable compositions of Examples 23 to 28 showed high bending strength and excellent ambient light stability, and no precipitation of aryliodonium salt was observed even after 90 days at 50° C., and the storage stability was excellent.

Comparative Examples 5 to 8

The dental photocurable compositions of Comparative Examples 5 and 6 had low bending strength and ambient light stability, and precipitation of aryliodonium salt was observed after 90 days at 50° C. It was confirmed that the dental photocurable compositions of Comparative Examples 7 and 8 had low bending strength, and that Comparative Example 8 had low ambient light stability.

TABLE 7

|  | Bending strength (MPa) | Ambient light stability (sec) | Storage stability Precipitation |
|---|---|---|---|
| Ex. 23 | 101 | 50 | A |
| Ex. 24 | 106 | 55 | A |
| Ex. 25 | 98 | 55 | A |

TABLE 7-continued

|  | Bending strength (MPa) | Ambient light stability (sec) | Storage stability Precipitation |
|---|---|---|---|
| Ex. 26 | 101 | 70 | A |
| Ex. 27 | 122 | 45 | A |
| Ex. 28 | 115 | 75 | A |
| Com. Ex. 5 | 74 | 10 | C |
| Com. Ex. 6 | 60 | 35 | B |
| Com. Ex. 7 | 47 | 55 | — |
| Com. Ex. 8 | 54 | 30 | — |

The symbol "-" in Table 7 indicates that the aryliodonium salt is not contained.

Examples 29 to 36

The dental photocurable compositions of Examples 29 to 36 had high adhesive strength, especially high durable adhesiveness, no precipitation of aryliodonium salt was observed even after 90 days at 50° C., and discoloration after immersion in water was extremely low. They had excellent storage stability.

Comparative Examples 9 and 10

The dental photocurable compositions of Comparative Examples 9 and 10 had low adhesive strength and color tone stability, and precipitation of aryliodonium salt was observed after 90 days at 50° C. From these results, the effectiveness of the aryliodonium salt having a specific structure was shown.

TABLE 8

|  | Adhesive strength (MPa) adhesive strength | Adhesive strength (MPa) Durable adhesive strength | Storage stability Precipitation | Discoloration $\Delta E$ |
|---|---|---|---|---|
| Ex. 29 | 20.4 | 22.4 | A | 0.5 |
| Ex. 30 | 21.1 | 20.1 | A | 1.2 |
| Ex. 31 | 19.4 | 20 | A | 2.8 |
| Ex. 22 | 15.7 | 16.3 | A | 2.3 |
| Ex. 33 | 25.3 | 23.8 | A | 1.1 |
| Ex. 34 | 18.4 | 22.6 | A | 1.9 |
| Ex. 35 | 19.9 | 14.5 | A | 2.2 |
| Ex. 36 | 18.4 | 18.3 | A | 2.5 |
| Com. Ex. 9 | 10.3 | 7.7 | C | 4.7 |
| Com. Ex. 10 | 4.5 | 2.2 | B | 7.2 |

In the above examples, the composite resin for dental filling, the dental resin cement, and the dental adhesive have been described, but the present invention can be used for other dental photocurable compositions without any restrictions.

The invention claimed is:
1. A photopolymerization initiator (c) used in a dental photocurable composition, comprising:
   (c-1) a photosensitizer,
   (c-2) a polymerization accelerator, and
   (c-3) an aryliodonium salt represented by the formula (1):

   (1)

wherein R1 represents a phenyl group which is bonded to I, wherein the phenyl group has at least one substituent selected from the group consisting of methyl, ethyl, propyl, butyl, octadecyl, isopropyl, isobutyl, sec-butyl, and tert-butyl, and wherein the R1 groups are the same or different from each other, R2 represents a fluorine substituted alkyl group selected from the group consisting of $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $(CF_3)_3C$, wherein the R2 groups are the same or different from each other, and b represents the number thereof which is an integer of from 1 to 5.

2. A dental photocurable composition comprising:
the photopolymerization initiator (c) according to claim 1, and
(a) a polymerizable monomer.

3. A dental photocurable composition comprising:
the photopolymerization initiator (c) according to claim 1,
(a) a polymerizable monomer, and
(b) a filler.

4. The dental photocurable composition according to claim 3, comprising the photopolymerization initiator (c) comprising:
(c-1) the photosensitizer: 0.1 to 5 parts by mass,
(c-2) the polymerization accelerator: 0.01 to 10 parts by mass, and
(c-3) the aryliodonium salt represented by the formula (1): 0.01 to 10 parts by mass, based on 100 parts by mass of the polymerizable monomer (a).

5. The dental photocurable composition according to claim 4, which comprises 10 to 1900 parts by weight of the filler (b), based on 100 parts by mass of the polymerizable monomer (a).

6. The dental photocurable composition according to claim 2, which is a dental adhesive, a dental composite resin, a dental abutment construction material, a dental resin cement, a dental surface covering material, a dental pit fissure sealing material, and/or a dental manicure material.

* * * * *